United States Patent
Fujisawa et al.

(10) Patent No.: US 7,071,274 B2
(45) Date of Patent: Jul. 4, 2006

(54) MONOMER, POLYMER, AND OCULAR LENS AND CONTACT LENS EACH OBTAINED THEREFROM

(75) Inventors: Kazuhiko Fujisawa, Otsu (JP); Naoki Shimoyama, Otsu (JP); Mitsuru Yokota, Otsu (JP)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 92 days.

(21) Appl. No.: 10/473,487

(22) PCT Filed: Mar. 11, 2002

(86) PCT No.: PCT/JP02/02231

§ 371 (c)(1),
(2), (4) Date: Sep. 29, 2003

(87) PCT Pub. No.: WO02/081485

PCT Pub. Date: Oct. 17, 2002

(65) Prior Publication Data

US 2004/0106694 A1 Jun. 3, 2004

(30) Foreign Application Priority Data

Mar. 30, 2001 (JP) ............................. 2001-100210

(51) Int. Cl.
*C08F 130/08* (2006.01)
(52) U.S. Cl. .................. 526/320; 526/279; 526/333
(58) Field of Classification Search ............... 526/279, 526/320, 333
See application file for complete search history.

(56) References Cited

U.S. PATENT DOCUMENTS 4,235,985 A * 11/1980 Tanaka et al. ............ 526/279
4,433,125 A    2/1984 Ichinohe et al.

FOREIGN PATENT DOCUMENTS

| GB | 2137635 A | * 10/1984 |
| JP | 61-281116 | * 12/1986 |
| JP | 03-286773 | * 12/1991 |

OTHER PUBLICATIONS

Silicone Hydrogels for Contact Lens Application, Jay F. Kunzler
Supplementary European Search Report, dated Dec. 30, 2004, for European Appln. No. EP 02702862.

* cited by examiner

*Primary Examiner*—Helen L. Pezzuto

(57) ABSTRACT

A monomer as represented by general formula (a) or (a') below, with which a polymer having high oxygen permeability and transparency and suited to an ophthalmic lens is obtained, is provided. Suitable monomers have the formula:

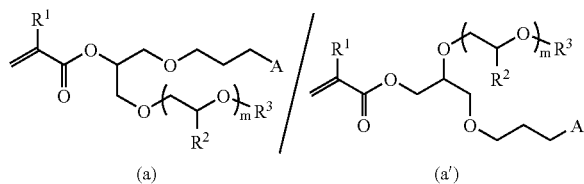

(a)                    (a')

wherein A is a siloxanyl group; $R^1$ and $R^2$ are H or methyl groups; $R^3$ is a substituted group that is selected from the group consisting of alkyl groups with 1 to 20 carbon atoms that may be substituted and aryl groups with 6 to 20 carbon atoms that may be substituted; m indicates an integer of 0 to 200.

9 Claims, No Drawings

MONOMER, POLYMER, AND OCULAR LENS AND CONTACT LENS EACH OBTAINED THEREFROM

This is a file under 35 U.S.C. 371 of PCT/JP02/02231 filed on Mar. 11, 2002, claiming the benefit of JP 2001-100210, filed on Mar. 30, 2001.

TECHNICAL FIELD

This invention relates to monomers and polymers. Said monomers and polymers are particularly suited to use for ophthalmic lenses such as contact lenses, intraocular lenses and artificial corneas.

PRIOR ART

Conventionally, monomers containing silicon groups are known as monomers for ophthalmic lenses. For example, 3-[tris(trimethylsiloxy)silyl] propyl methacrylate has been widely used as monomers for ophthalmic lenses. Polymers obtained by copolymerizing this 3-[tris(trimethylsiloxy)silyl] propyl methacrylate with N,N-dimethylacrylamide, which is a hydrophilic monomer, have the merits of being transparent and of having high oxygen permeability. However, sufficient compatibility is not obtained with three component copolymers in which a silicone macromer such as polydimethylsiloxane having a methacryl group in the terminal is added in order to obtain high oxygen permeability and rubber elasticity. For this reason, when they are used as contact lenses, for example, there are instances in which the contact lenses are turbid.

DISCLOSURE OF THE INVENTION

This invention has the objective of providing monomers and polymers, ophthalmic lenses and contact lenses in which they are used, in which the polymers that are obtained by polymerization are of high oxygen permeability and which have sufficient compatibility in three-component systems of silicone macromers/hydrophilic monomers.

In order to achieve the aforementioned objectives, this invention has the following structure.

(1) A monomer comprising a polymerizable unsaturated double bond and siloxanyl group, wherein said monomer comprises a hydrophilic group in a side chain.

(2) The monomer of (1) above wherein the hydrophilic group is selected from an ether bond and/or polyalkylene glycol chain.

(3) A monomer that is represented by general formula (a) or (a'):

(a) (a')

wherein A is a siloxanyl group; $R^1$ and $R^2$ are H or methyl groups; $R^3$ is a substituted group that is selected from the group consisting of alkyl groups with 1 to 20 carbon atoms that may be substituted and aryl groups with 6 to 20 carbon atoms that may be substituted; m indicates an integer of 0 to 200.

(4) The monomer of (3) above wherein the siloxanyl group (A) in formula (a) or (a') is a substituted group as represented by formula (b) below:

(b)

wherein in formula (b), $A^1$ to $A^{11}$, independently and respectively, are selected from H, alkyl groups of 1 to 20 carbon atoms that may be substituted or aryl groups of 6 to 20 carbon atoms that may be substituted; n is an integer of 0 to 200 and a, b and c, independently and respectively, indicate integers of 0 to 20, provided that the case where all of n, a, b and c denote zero is to be eliminated.

(5) The monomer of (3) above wherein the siloxanyl group (A) in the aforementioned general formula (a) or (a') is a substituted group selected from tris(trimethylsiloxy)silyl groups, bis(trimethylsiloxy)methylsilyl groups and trimethylsiloxydimethylsilyl groups.

(6) A polymer comprising the monomer described in either of (1) or (3) above as a polymerization component.

(7) The polymer of (6) above wherein a ratio of the hydrophilic side chain to the siloxanyl group is 0.1 to 1.

(8) A polymer which is a homopolymer of the monomer described in either (1) or (3) above.

(9) A polymer comprising the monomer described in either (1) or (3) above in a range of 10% to 80% as a polymerization component.

(10) An ophthalmic lens which comprises the polymer described in (6) above.

(11) A contact lens which comprises the polymer described in (6) above.

EMBODIMENT OF THE INVENTION

First, we shall describe the various functional groups in the monomers. The polymerizable unsaturated double bond may be any double bond as long as it can produce polymers by radical polymerization. Examples of groups that can be used include (meth)acryloyl groups, styryl groups, benzoyl groups and vinyl groups. Of these, the use of methacryloyl groups is desirable from the standpoints of ease of synthesis and polymerizability.

The term siloxanyl group indicates a group that has at least one Si—O—Si bond. The use of substituted groups represented by formula (b) below as the siloxanyl groups is desirable from the standpoints of ease of acquisition of raw materials and ease of synthesis.

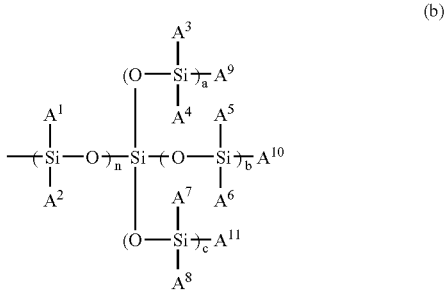

(b)

[In formula (b), $A^1$ to $A^{11}$, independently and respectively, indicate H, alkyl groups of 1 to 20 carbon atoms that may be substituted or aryl groups of 6 to 20 carbon atoms that may be substituted. n indicates an integer of 0 to 200 and a, b and c, independently and respectively, indicate integers of 0 to 20, provided that the case where all of n, a, b and c denote zero is to be eliminated.]

The hydrophilic groups of this invention are introduced to mitigate the water-repellency of the monomers of this invention and to increase their hydrophilic properties. Polyalkylene glycol chains and ether bonds can be cited as desirable examples of them.

In order to further facilitate understanding of the nature of this invention, we shall now describe the various substituted groups in general formula (a) or (a') more specifically.

In formula (b), which illustrates the siloxanyl groups of A, $A^1$ to $A^{11}$, independently and respectively, indicate H, alkyl groups such as methyl groups, ethyl groups, propyl groups, isopropyl groups, butyl groups, isobutyl groups, sec-butyl groups, t-butyl groups, hexyl groups, cyclohexyl groups, 2-ethylhexyl groups and octyl groups and aryl groups such as phenyl groups and naphthyl groups. Examples of alkyl groups and aryl groups that may be substituted can include 3-glycidoxypropyl groups, 2-hydroxyethoxypropyl groups, 3-hydroxypropyl groups, 3-aminopropyl groups and fluorophenyl groups. Of these, methyl groups are the most desirable.

In formula (b), n is an integer of 0 to 200, preferably, of 0 to 50, and, more preferably, of 0 to 10. a, b and c are, respectively and individually, integers of 0 to 20, and, preferably, a, b and c are, respectively and individually, integers of 0 to 5. When n=0, desirable combinations of a, b and c are a=b=c=1, a=b=1 and c=0.

Of the substituted groups represented by formula (b), those that are particularly desirable from the standpoint that they can be acquired industrially comparatively cheaply are tris(trimethylsiloxy) silyl groups, bis(trimethylsiloxy)methylsilyl groups, trimethylsilyoxydimethylsilyl groups, tris(3-hydroxypropyldimethylsiloxy)silyl groups, bis(3-hydroxypropyldimethylsiloxy)methylsilyl groups, tris[3-(2-hydroxyethoxy)propyldimethylsiloxy)silyl groups, bis[3-(2-hydroxyethoxy)propyldimethylsiloxy)methylsilyl groups, polydimethylsiloxane groups, polymethylsiloxane groups and poly-co-methylsiloxane-dimethylsiloxane groups.

In formula (a) or (a'), $R^3$ indicates a substituted group selected from a group comprised of alkyl groups of 1 to 20 carbon atoms that may be substituted and aryl groups of 6 to 20 carbon atoms that may be substituted. Desirable examples include methyl groups, ethyl groups, propyl groups, butyl groups, pentyl groups, hexyl groups, heptyl groups, octyl groups, decyl groups, cyclohexyl groups, benzyl groups, phenyl groups and naphthyl groups. Of these, methyl groups, ethyl groups and phenyl groups are preferable, and methyl groups are most preferable.

In formula (a) or (a'), the component below indicates the hydrophilic group.

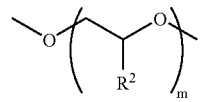

m indicates an integer of 0 to 200. When m increases, the hydrophilic property becomes stronger. However, the balance with high oxygen permeability deteriorates, for which reason it should be 0 to 50, and, more preferably, 0 to 20, in order to obtain a good balance of physical properties.

The polymers of this invention can be obtained by polymerizing the monomers of this invention individually and they can also be obtained by copolymerization with other monomers. There are no particular limitations on the other monomers that are copolymerized as long as they can be copolymerized, and monomers that have (meth)acryloyl groups, styryl groups, allyl groups, vinyl groups and other polymerizable carbon-carbon unsaturated bonds can be used.

Several examples are presented below. However, this invention is not limited to them. One group includes hydrophilic monomer groups comprised of (meth)acrylic acid, itaconic acid, crotonic acid, vinyl benzoic acid, (meth) acrylamides such as N,N-dimethylacrylamide and N-vinyl lactams such as N-vinyl pyrrolidone. Another group of examples is a hydrophobic monomer group including alkyl (meth)acrylates such as methyl(meth)acrylate and aromatic vinyl monomers such as styrene. Further, monomers having oxygen permeability include (meth)acrylates containing fluoroalkyl groups, silicone macromers such as polydimethylsiloxane having (meth)acryloyl groups in the terminals and 3-[tris(trimethylsiloxy)silyl] propylmethacrylate.

The (co)polymerization ratio of monomers represented by general formula (a) or (a') in the polymers of this invention, in the case in which they do not include monomers containing silicon groups and from the standpoint of establishing both high oxygen permeability and high hydrophilic properties, should be 30 to 100 weight %, preferably, 40 to 99 weight %, and, more preferably, 50 to 95 weight %.

In copolymerization with oxygen permeable monomers, it is desirable that the total for the monomers of this invention and other oxygen permeable monomers be within the range of the aforementioned copolymerization ratio. Further, in this case, when the proportion of siloxanyl groups is excessively high, it is difficult to assure balance between wettability and oxygen permeability, for which reason, it is necessary to set the hydrophilic group/siloxanyl ratio in the polymer above a fixed value. That is, it is necessary that it be from 0.1 to 1. Values from 0.3 to 0.7 are particularly desirable.

For the purpose of obtaining good mechanical properties and of obtaining good resistance to disinfecting solutions and cleaning solutions, it is desirable to use monomers having two or more copolymerizable carbon-carbon unsaturated bonds in one molecule, in the polymers of this invention. The copolymerization ratio of the monomers having two or more copolymerizable carbon-carbon unsaturated bonds in one molecule should be greater than 0.1 weight %, preferably, greater than 0.3 weight %, and, more preferably, greater than 0.5 weight %. Their weight, when the monomers of this invention are polymerized by themselves, and the total weight of the copolymerization monomers with the monomers of this invention when they are copolymerized with other monomers are taken as 100 weight %. The same holds hereafter.

The polymer of this invention may also contain ultraviolet absorbents, pigments and colorants. It may also contain ultraviolet absorbents, pigments and colorants having polymerizable groups in the form that they are copolymerized.

In order to facilitate polymerization when the polymers of this invention are obtained by polymerization, the addition of thermal polymerization initiators and photopolymerization initiators of which peroxides and azo compounds are representative is desirable. When thermal polymerization is performed, a substance having optimum decomposition characteristics at the desired reaction temperature is selected and used. In general, azo initiators and peroxide initiators having 10 hour half-life temperatures of 40° C. to 120° C. are suitable. Carbonyl compounds, peroxides, azo compounds, sulfur compounds, halogen compounds and metal salts can be cited as photopolymerization initiators. These polymerization initiators can be used individually or in mixtures and are used in quantities up to approximately 1 weight %.

A polymerization solvent can be used when the polymers of this invention are obtained by polymerization. Various organic and inorganic solvents can be used as the solvents and there are no particular limitations on them. Examples that can be cited include water, various alcohol solvents such as methanol, ethanol, propanol, 2-propanol, butanol and tert-butanol, various aromatic hydrocarbon solvents such as benzene, toluene and xylene, various aliphatic hydrocarbon solvents such as hexane, heptane, octane, decane, petroleum ether, kerosene, ligroin and paraffin, various ketone solvents such as acetone, methyl ethyl ketone and methyl isobutyl ketone, various ester solvents such as ethyl acetate, butyl acetate, methyl benzoate and dioctyl phthalate and various glycol ether solvents such as diethyl ether, tetrahydrofuran, dioxane, ethylene glycol dialkyl ethers, diethylene glycol dialkyl ethers, triethylene glycol dialkyl ethers, tetraethylene glycol dialkyl ethers and polyethylene glycol dialkyl ethers. They can be used individually or in mixtures.

Usual methods can be used as the polymerization methods and molding methods of the polymers of this invention. They include, for example, a method in which they are molded into rods or plates and are then processed to the desired shapes by cutting and processing, a mold polymerization method and a spin cast method. As an example, we shall now describe the case in which the polymer of this invention is obtained by the mold polymerization method.

The monomer composition is filled into the space of two molds having a fixed shape. Photopolymerization or thermal polymerization is performed and it is formed to the shape of the mold. The mold can be made of resin, glass, ceramics or metal. In the case of photopolymerization, a material that is optically transparent is used, and, ordinarily, resin or glass is used. In many cases, when a polymer is manufactured, a space is formed by the two opposing molds and the space is filled with the monomer composition. Depending on the shape of the mold and the properties of the monomer, a gasket may be used for the purpose of conferring a fixed thickness on the polymer and of preventing leakage of the filled monomer composition solution. The mold into the space of which the monomer composition is filled is then irradiated with active light rays such as ultraviolet rays or is introduced into an oven or a water bath or oil bath and is heated to polymerize the monomers. The two methods can also be used in combination, with thermal polymerization being performed after photopolymerization, or, conversely, it can be photopolymerization being performed after thermal polymerization. In the case of photopolymerization, for example, light containing a large portion of ultraviolet rays is usually irradiated for a short time (ordinarily 1 hour or less) using a mercury lamp or an insect attraction lamp as the light source. When thermal polymerization is performed, the temperature is gradually raised from close to room temperature, being increased to a temperature of 60° C. to 200° C. over a period of several hours to several tens of hours. These conditions are desirable for the purpose of maintaining the optical homogeneity and quality of the polymer and of increasing reproducibility.

The molded product in which the polymer of this invention is used can be subjected to modification treatments by various methods. It is desirable to perform said modification treatment for the purpose of increasing surface wettability.

Specific modification methods can include electromagnetic waves (including light) irradiation, plasma irradiation, chemical vapor deposition treatments such as vaporization and sputtering, heating treatments, treatment with bases, treatment with acids and the use of other suitable surface treatment agents, and combinations of these treatments. Of these modification procedures, treatment with bases and treatment with acids are desirable because they are simple.

Examples of treatments with bases and treatments with acids that can be cited include a method in which the molded product is brought into contact with a basic or acidic solution and a method in which the molded product is brought into contact with a basic or acidic gas. More specific examples include, for example, a method in which the molded product is immersed in a basic or acidic solution, a method in which a basic or acidic solution or basic or acidic gas is sprayed at the molded product, a method in which the basic or acidic solution is applied to the molded product with a spatula or brush and a method in which the basic or acidic solution is applied to the molded product by the spin coating method or the dip coating method. The method whereby great modifying effects can be obtained the most simply is the method in which the molded product is immersed in a basic or acidic solution.

There are no particular limitations on temperature when the molded product is immersed in the basic or acidic solution. However, the procedure is usually performed in a temperature range of −50° C. to 300° C. When workability is considered, a temperature range of −10° C. to 150° C. is preferable and −5° C. to 60° C. is more preferable.

The optimum period for immersion of the molded product in the basic or acidic solution varies depending on the temperature. In general, a period of up to 100 hours is desirable, a period of up to 24 hours is more preferable and a period of up to 12 hours is most preferable. When contact time is too long, workability and productivity deteriorate and there are instances in which there are such deleterious effects as decrease of oxygen permeability and decrease of mechanical properties.

The bases that can be used include alkali metal hydroxides, alkaline earth metal hydroxides, various carbonates, various borates, various phosphates, ammonia, various ammonium salts, various amines and high molecular weight bases such as polyethylene imines and polyvinyl amines. Of these, alkali metal hydroxides are the most desirable because of their low cost and their great treatment effectiveness.

The acids that can be used include various inorganic acids such as sulfuric acid, phosphoric acid, hydrochloric acid and nitric acid, various organic acids such as acetic acid, formic acid, benzoic acid and phenol and various high molecular weight acids such as polyacrylic acids and polystyrene sulfonic acids. Of these, high molecular weight acids are the most desirable because they have great treatment effectiveness and have little deleterious effect on other physical properties.

Various inorganic and organic solvents can be used as solvents of the basic and acidic solutions. For example, they can include water, various alcohols such as methanol, ethanol, propanol, 2-propanol, butanol, ethylene glycol, diethylene glycol, triethylene glycol, tetraethylene glycol, polyethylene glycol and glycerol, various aromatic hydrocarbons such as benzene, toluene and xylene, various aliphatic hydrocarbons such as hexane, heptane, octane, decane, petroleum ether, kerosene, ligroin and paraffin, various ketones such as acetone, methyl ethyl ketone and methyl isobutyl ketone, various esters such as ethyl acetate, butyl acetate, methyl benzoate and dioctyl phthalate, various ethers such as diethyl ether, tetrahydrofuran, dioxane, ethylene glycol dialkyl ether, diethylene glycol dialkyl ether, triethylene glycol dialkyl ether, tetraethylene glycol dialkyl ether and polyethylene glycol dialkyl ether, various nonprotonic polar solvents such as dimethylformamide, dimethylacetamide, N-methyl-2-pyrrolidone, dimethylimidazolidinone, hexamethyl phosphoric triamide and dimethyl sulfoxide, halogen solvents such as methylene chloride, chloroform, dichloroethane, trichloroethane and trichloroethylene and freon solvents. Of these, water is the most desirable from the standpoints of economic factors, convenience of handling and chemical stability. These solvents can also be used in mixtures of two or more.

The basic or acidic solution that is used in this invention may also contain components other than the basic or acidic substances and the solvents.

After the molded product has been subjected to treatment with bases or acids, the basic or acidic substance can be removed by washing.

Various inorganic and organic solvents can be used as washing solvents. For example, they can include water, various alcohols such as methanol, ethanol, propanol, 2-propanol, butanol, ethylene glycol, diethylene glycol, triethylene glycol, tetraethylene glycol, polyethylene glycol and glycerol, various aromatic hydrocarbons such as benzene, toluene and xylene, various aliphatic hydrocarbons such as hexane, heptane, octane, decane, petroleum ether, kerosene, ligroin and paraffin, various ketones such as acetone, methyl ethyl ketone and methyl isobutyl ketone, various esters such as ethyl acetate, butyl acetate, methyl benzoate and dioctyl phthalate, various ethers such as diethyl ether, tetrahydrofuran, dioxane, ethylene glycol dialkyl ether, diethylene glycol dialkyl ether, triethylene glycol dialkyl ether, tetraethylene glycol dialkyl ether and polyethylene glycol dialkyl ether, various nonprotonic polar solvents such as dimethylformamide, dimethylacetamide, N-methyl-2-pyrrolidone, dimethylimidazolidinone, hexamethyl phosphoric triamide and dimethyl sulfoxide, halogen solvents such as methylene chloride, chloroform, dichloroethane trichloroethane and trichloroethylene and freon solvents.

Mixtures of two or more of these solvents can be used as the washing solvent. The washing solvent may contain components other than the solvents, for example, inorganic salts, surfactants and detergents.

The entire molded product may be subjected to said modification treatment or it may be performed on only a portion of the molded product, for example, the surface. When only the surface is subjected to modification treatment, the aqueous wetting property of the surface can be improved without making great changes in the physical properties of the molded product as a whole.

The polymers of this invention should have an oxygen permeability coefficient greater than $70 \times 10^{-11}$ $(cm^2/sec)$ $mLO_2/(mL \cdot hPa)$ in terms of the oxygen permeability.

The polymers of this invention are particularly suited for ophthalmic lenses such as contact lenses, intraocular lenses and artificial corneas.

EXAMPLES

We shall now describe this invention in specific terms by means of examples. However, this invention is not limited by them.

Determination Methods

The various determinations in these examples were performed by the methods described below.

(1) Proton Nuclear Magnetic Resonance Spectrum

Determinations were performed using a model EX270 manufactured by JEOL Ltd. Chloroform-d was used as the solvent.

(2) Gas Chromatography (GC)

A capillary column (TC-5HT) manufactured by GL Sciences, Inc. was used with a model GC-18A manufactured by SHIMADZU CORPORATION. Determinations were made with a temperature elevation program in which the temperature was maintained at 100° C. for 1 minute, after which the temperature was raised to 340° C. at a rate of 10° C./minute and then maintained at 340° C. for 5 minutes (introduction inlet temperature, 340° C.; detection temperature, 360° C.).

(3) Oxygen Permeability Coefficient

The oxygen permeability coefficient of a sample in the shape of a contact lens was determined in water of 35° C. using a Seikaken-shiki film oxygen permeability meter manufactured by RIKA SEIKI KOGYO Co., Ltd.

Example 1

(1) 30 g (89 mmol) of 3-(glycidyloxypropyl)-1,1,1,3,5,5,5-hexamethyltrisiloxane, 90 g of 2-methoxyethanol and 1.14 g (9 mmol) of tetracyanoethylene (TCNE) were added to a 200 mL eggplant type distillation flask and the mixture was stirred for 3 hours, after which it was allowed to stand overnight at room temperature. After the reaction was completed, the solvent was removed using an evaporator. The proton nuclear magnetic resonance spectrum of the liquid that was obtained was determined and analyzed. As a result, peaks were detected in the vicinity of 0 ppm (3H), in the vicinity of 0.1 ppm (18H), in the vicinity of 0.4 ppm (2H), in the vicinity of 1.5 ppm (2H), in the vicinity of 2.6 ppm (1H), in the vicinity of 3.3 to 3.7 ppm (13H) and in the vicinity of 3.9 ppm (1H). From these findings, it was confirmed that it was a mixture of the compounds represented by formulas (M1) and (M1') below. On the basis of the GC peak area ratios, the (M1)/(M1') ratio was 85/15.

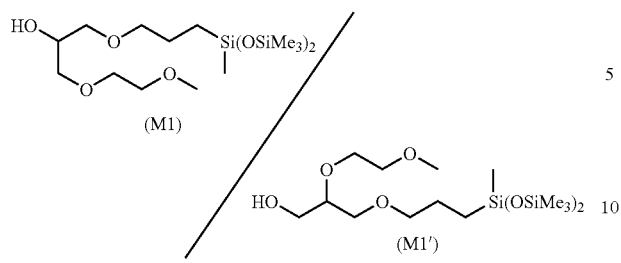

(2) 30 g (73 mmol) of the compound obtained in (1) above was transferred, 80 g of ethyl acetate and 8.83 g (87 mmol) of triethylamine were added to a 300 mL eggplant type distillation flask, and 9.12 g (87 mmol) of methacrylic acid chloride was added dropwise at 0° C. After the dropwise additions were completed, the reaction solution was stirred for 3 hours as it was being restored to room temperature. The reaction solution was filtered and the precipitate was removed, after which it was transferred to a separatory funnel as it was being washed with ethyl acetate. It was then washed with saturated sodium hydrogencarbonate and saturated saline solution and dried with sodium sulfate. The solvent was removed with an evaporator and purification was performed by distillation under reduced pressure. The proton nuclear magnetic resonance spectrum of the liquid that was obtained was determined and analyzed. As a result, peaks were detected in the vicinity of 0 ppm (3H), in the vicinity of 0.1 ppm (18H), in the vicinity of 0.4 ppm (2H), in the vicinity of 1.5 ppm (2H), in the vicinity of 1.9 ppm (3H), in the vicinity of 2.6 ppm (1H), in the vicinity of 3.3 ppm (5H), in the vicinity of 3.4 to 3.7 ppm (8H), in the vicinity of 4.2 ppm (0.2H), in the vicinity of 5.1 ppm (0.8H), in the vicinity of 5.5 ppm (1H) and in the vicinity of 6.1 ppm (1H). From these findings, it was confirmed that it was a mixture of the compounds represented by formulas (M2) and (M2') below. On the basis of the GC peak area ratios, the (M2)/(M2') ratio was 85/15.

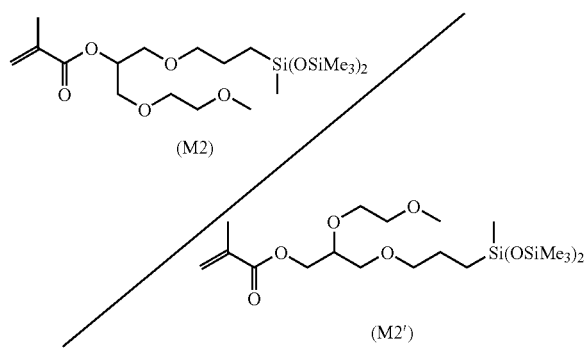

Example 2

Synthesis was performed in the same way as in Example 1 using 2-(2-methoxyethoxy)ethanol instead of 2-methoxyethanol and a silica gel column instead of distillation under reduced pressure as the purification method. The proton nuclear magnetic resonance spectrum of the liquid that was obtained was determined and analyzed. As a result, peaks were detected in the vicinity of 0 ppm (3H), in the vicinity of 0.1 ppm (18H), in the vicinity of 0.4 ppm (2H), in the vicinity of 1.5 ppm (2H), in the vicinity of 1.9 ppm (3H), in the vicinity of 3.3 ppm (5H), in the vicinity of 3.4 to 3.7 ppm (12H), in the vicinity of 4.2 ppm (0.1H), in the vicinity of 5.1 ppm (0.9H), in the vicinity of 5.5 ppm (1H) and in the vicinity of 6.1 ppm (1H). From these findings, it was confirmed that it was a mixture of the compounds represented by formulas (M3) and (M3') below. On the basis of the GC peak area ratios, the (M3)/(M3') ratio was 86/14.

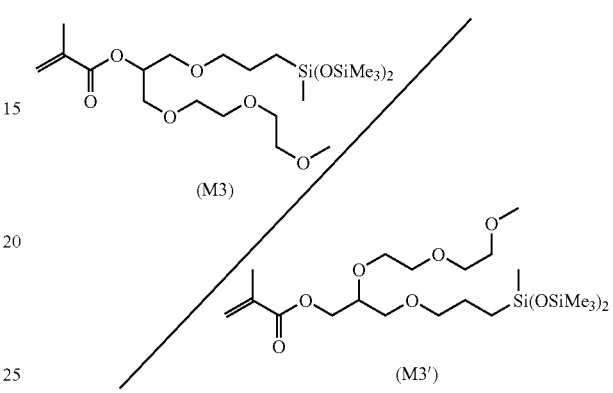

Example 3

(1) 50 g (0.44 mol) of allyl glycidyl ether, 100 g (3.12 mol) of methanol and 5.61 g (0.044 mol) of tetracyanoethylene were added to a 300 mL eggplant type distillation flask and the mixture was stirred for 3 hours at room temperature, after which it was allowed to stand overnight. After the reaction was completed, the solvent was removed using an evaporator and the liquid that was obtained was purified by distillation under reduced pressure. The proton nuclear magnetic resonance spectrum of the liquid that was obtained was determined and analyzed. As a result, peaks were detected in the vicinity of 2.4 ppm (1H), in the vicinity of 3.4 ppm (7H), in the vicinity of 3.6 ppm (0.3H), in the vicinity of 3.9 ppm (2.7H), in the vicinity of 5.2 ppm (2H) and in the vicinity of 5.8 ppm (1H). From these findings, it was confirmed that it was a mixture of the compounds represented by formulas (M4) and (M4') below. On the basis of the GC peak area ratios, the (M4)/(M4') ratio was 73/27.

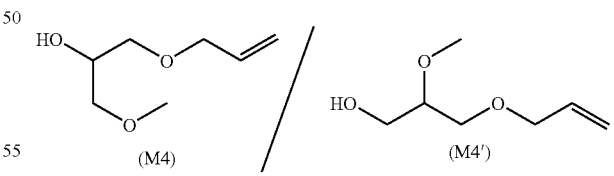

(2) 50 g (0.34 mol) of the compound obtained in (1) above, 80 g of ethyl acetate and 41.53 g (0.41 mol) of triethylamine were added to a 300 mL eggplant type distillation flask and 42.91 g (0.41 mol) of methacrylic acid chloride was added dropwise at 0° C. The reaction solution was restored to room temperature as it was being stirred over a period of 3 hours. It was transferred to a separatory funnel as it was being washed with ethyl acetate. It was then washed with saturated sodium hydrogencarbonate and saturated saline solution and dried with sodium sulfate. The solvent was removed with an evaporator and the liquid that was obtained was purified by distillation under reduced pressure. The proton nuclear magnetic resonance spectrum of the liquid that was obtained was determined and analyzed. As a result, peaks were detected in the vicinity of 1.9 ppm (3H), in the vicinity of 3.3 ppm (3H), in the vicinity of 3.6 ppm (4H), in the vicinity of 3.9 ppm (2H), in the vicinity of 4.2 ppm (0.3H), in the vicinity of 5.2 ppm (2.7H), in the vicinity of 5.5 ppm (1H), in the vicinity of 5.8 ppm (1H) and in the vicinity of 6.1 ppm (1H). From these findings, it was confirmed that it was a mixture of the compounds represented by formulas (M5) and (M5') below. On the basis of the GC peak area ratios, the (M5)/(M5') ratio was 82/18.

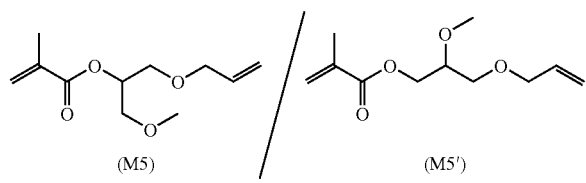

(M5) / (M5')

(3) 40 g (0.19 mol) of the compound obtained in (2) above, 100 mL of toluene, 41.1 mg (0.19 mmol) of BHT and 96.7 mg (0.19 mmol) of chloroplatinic (IV) acid 6-hydrate were added to a 300 mL eggplant type distillation flask and 25.29 g (0.19 mol) of trichlorosilane was added dropwise as the mixture was being stirred. The reaction solution was stirred over night at room temperature, after which the solvent was removed with an evaporator and purification was performed by distillation under reduced pressure.

A mixture obtained by adding 118.56 g (1.14 mol) of methoxytrimethylsilane to the liquid that was obtained was transferred to a dropping funnel and was added dropwise to a mixed solvent of water-methanol-hexane (40 mL-20 mL-20 mL) that had been cooled to 0° C. The reaction solution was stirred overnight at room temperature, after which the aqueous layer was discarded, the organic layer was washed with saturated sodium hydrogencarbonate and saturated saline solution and dried with sodium sulfate. The liquid that was obtained was purified by distillation under reduced pressure. The proton nuclear magnetic resonance spectrum of the liquid that was obtained was determined and analyzed. As a result, peaks were detected in the vicinity of 0.1 ppm (27H), in the vicinity of 0.4 ppm (2H), in the vicinity of 1.5 ppm (2H), in the vicinity of 1.9 ppm (3H), in the vicinity of 3.4 ppm (5H), in the vicinity of 3.5 ppm (4H), in the vicinity of 4.2 ppm (0.2H), in the vicinity of 5.1 ppm (0.8H), in the vicinity of 5.5 ppm (1H) and in the vicinity of 6.1 ppm (1H). From these findings, it was confirmed that it was a mixture of the compounds represented by formulas (M6) and (M6') below. On the basis of the GC peak area ratios, the (M6)/(M6') ratio was 83/17.

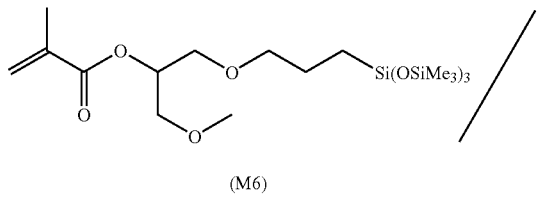

(M6)

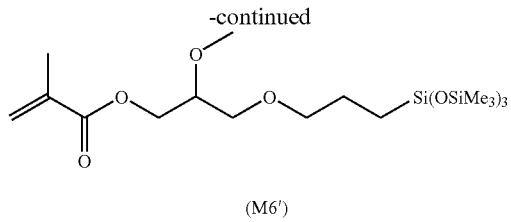

(M6')

Example 4

Synthesis was performed in the same way as in Example 3 using ethanol instead of methanol. The proton nuclear magnetic resonance spectrum of the liquid that was obtained was determined and analyzed. As a result, peaks were detected in the vicinity of 0.1 ppm (27H), in the vicinity of 0.4 ppm (2H), in the vicinity of 1.2 ppm (3H), in the vicinity of 1.5 ppm (2H), in the vicinity of 1.9 ppm (3H), in the vicinity of 3.4 ppm (4H), in the vicinity of 3.5 ppm (4H), in the vicinity of 4.2 ppm (0.2H), in the vicinity of 5.1 ppm (0.8H), in the vicinity of 5.5 ppm (1H) and in the vicinity of 6.1 ppm (1H). From these findings, it was confirmed that it was a mixture of the compounds represented by formulas (M7) and (M7') below. On the basis of the GC peak area ratios, the (M7)/(M7') ratio was 82/18.

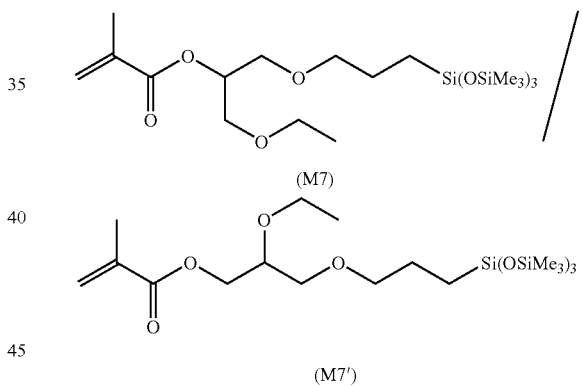

(M7)

(M7')

Example 5

Synthesis was performed in the same way as in Example 3 using 1-propanol instead of methanol. The proton nuclear magnetic resonance spectrum of the liquid that was obtained was determined and analyzed. As a result, peaks were detected in the vicinity of 0.1 ppm (27H), in the vicinity of 0.4 ppm (2H), in the vicinity of 0.9 ppm (3H), in the vicinity of 1.5 ppm (2H), in the vicinity of 1.6 ppm (2H), in the vicinity of 1.9 ppm (3H), in the vicinity of 3.4 ppm (4H), in the vicinity of 3.5 ppm (4H), in the vicinity of 4.2 ppm (0.2H), in the vicinity of 5.1 ppm (0.8H), in the vicinity of 5.5 ppm (1H) and in the vicinity of 6.1 ppm (1H). From these findings, it was confirmed that it was a mixture of the compounds represented by formulas (M8) and (M8') below. On the basis of the GC peak area ratios, the (M8)/(M8') ratio was 85/15.

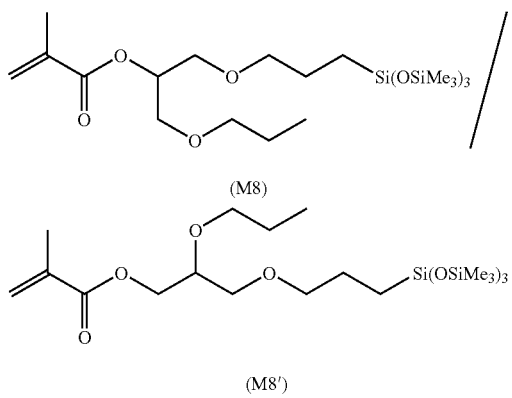

(M8)

(M8')

Example 6

The mixture of compounds of formulas (M2) and (M2') obtained in Example 1 (30 parts by weight), N,N-dimethylacrylamide (40 parts by weight), polydimethylsiloxane of which the terminals had been methacrylated (molecular weight, approximately 1,000; 30 parts by weight), triethylene glycol dimethacrylate (1 part by weight) and Darocure 1173 (CIBA Specialty Chemicals Inc.; 0.2 part by weight) were mixed and stirred. A homogeneous and transparent monomer mixture was obtained. This monomer mixture was deaerated in an argon atmosphere. It was poured into a contact lens mold made of a transparent resin (poly 4-methylpentene-1) in a glove box in a nitrogen atmosphere and was polymerized by light irradiation (1 mW/cm², 10 minutes) using an insect attraction lamp, and a sample in the shape of a contact lens was obtained.

The lens-shaped sample that was obtained was subjected to hydration treatment, after which it was immersed in a 5 weight % aqueous solution of polyacrylic acid (molecular weight, approximately 150,000) and modification treatment was performed for 8 hours at 40° C. After the modification treatment, it was washed thoroughly with purified water and immersed in a boric acid buffer solution (pH 7.1 to 7.3) in a vial and the vial was hermetically sealed. Said vial was introduced into an autoclave and boiling treatment was performed for 30 minutes at 120° C. After it had cooled, the lens-shaped sample was removed from the vial and was immersed in a boric acid buffer solution (pH 7.1 to 7.3).

The sample that was obtained was transparent and not turbid. When this sample was subjected to hydration treatment, its oxygen permeability coefficient was $79 \times 10^{-11}$ $(cm^2/sec)mLO_2/(mL \cdot hPa)$. Thus, it had high transparency and high oxygen permeability.

Examples 7 to 10

The monomer mixtures obtained in Examples 2 to 6 were used and contact lens-shaped samples were obtained by the same method as in Example 7. All of the samples that were obtained were transparent and they were not turbid. The oxygen permeability coefficients $[\times 10^{-11}$ $(cm^2/sec)mLO_2/(mL \cdot hPa)]$ when these samples were subjected to hydration treatment are shown in Table 1. All of the polymers were of high transparency and oxygen permeability.

TABLE 1

|  | Oxygen permeability coefficient<br>$[\times 10^{-11}$ $(cm^2/sec)mLO_2/(mL \cdot hpa)]$ |
|---|---|
| Example 7 | 78 |
| Example 8 | 76 |
| Example 9 | 75 |
| Example 10 | 74 |

Comparative Examples

When a monomer mixture was prepared at the same molar ratio as in Example 7 using 3-tris(trimethylsiloxy)silylpropyl methacrylate, the substances did not mix sufficiently and separated from each other. This monomer mixture was polymerized by light irradiation in the same way as in Example 7, but a transparent contact lens-shaped sample was not obtained.

INDUSTRIAL APPLICABILITY

By means of this invention, monomers are provided so that the polymers that are obtained by polymerizing them are of high oxygen permeability and transparency.

The invention claimed is:

1. A monomer that is represented by general formula (a) or (a') below:

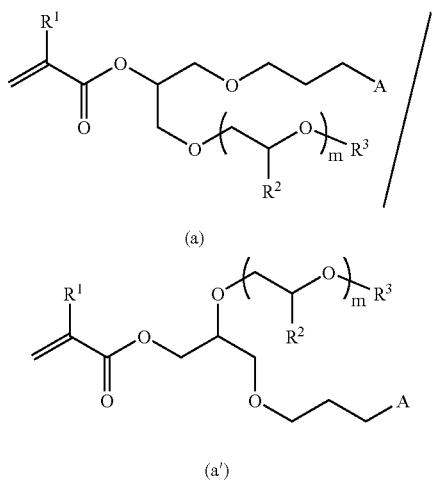

(a)

(a')

wherein A is a siloxanyl group; $R^1$ and $R^2$ are H or methyl groups; $R^3$ is a substituted group that is selected from the group consisting of alkyl groups with 1 to 20 carbon atoms that may be substituted and aryl groups with 6 to 20 carbon atoms that may be substituted; m indicates an integer of 0 to 200.

2. The monomer of claim 1 wherein the siloxanyl group (A) in formula (a) or (a') is a substituted group as represented by formula (b) below:

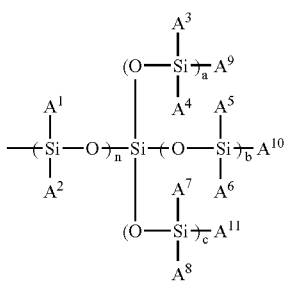

(b)

wherein, in formula (b), $A^1$ to $A^{11}$, independently and respectively, are H, alkyl groups of 1 to 20 carbon atoms that may be substituted or aryl groups of 6 to 20 carbon atoms that may be substituted; n is an integer of 0 to 200 and a, b and c, independently and respectively, indicate integers of 0 to 20, provided that the case where all of n, a, b and c denote zero is to be eliminated.

3. The monomer of claim 1 wherein the siloxanyl group (A) in the aforementioned general formula (a) or (a') is a substituted group selected from tris(trimethylsiloxy)silyl groups, bis(trimethylsiloxy)methylsilyl groups and trimethylsiloxydimethylsilyl groups.

4. A polymer comprising the monomer set forth in claim 1 as a polymerization component.

5. The polymer of claim 4 wherein a ratio of the hydrophilic side chain to the siloxanyl group is 0.1 to 1.

6. A polymer that is a homopolymer of the monomer set forth in claim 1.

7. A polymer comprising the monomer set forth in claim 1 in a range of 10% to 80% as a polymerization component.

8. An ophthalmic lens which comprises the polymer set forth in claim 4.

9. A contact lens which comprises the polymer set forth in claim 4.

* * * * *